Figure 1:
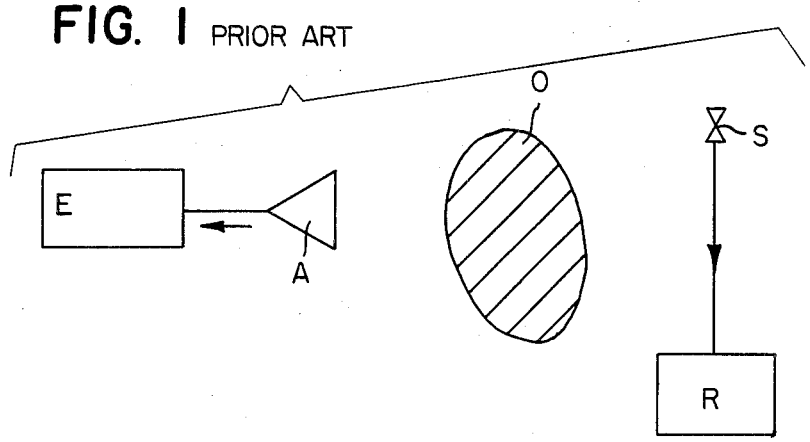

United States Patent [19]

Bolomey et al.

[11] Patent Number: 4,552,151
[45] Date of Patent: Nov. 12, 1985

[54] PROCESS AND MEANS FOR RAPID POINT BY POINT SURVEY OF BODY SCANNING RADIATION FIELD

[75] Inventors: Jean-Charles Bolomey, Sceaux; Yves Michel, Massy, both of France

[73] Assignees: Centre National de la Recherche Scientifique, Paris; Societe d'Etude du Radant, Les Ulis, both of France

[21] Appl. No.: 677,897

[22] Filed: Dec. 5, 1984

Related U.S. Application Data

[63] Continuation-in-part of Ser. No. 394,986, Jul. 2, 1982.

[30] Foreign Application Priority Data

Jul. 2, 1981 [FR] France ................. 81 13005

[51] Int. Cl.[4] .............................................. A61B 5/04
[52] U.S. Cl. ...................................... 128/653; 343/754
[58] Field of Search ........ 343/754; 324/58 A, 58.5 A; 128/653

[56] References Cited

U.S. PATENT DOCUMENTS

| 3,265,967 | 8/1966 | Heald | 324/58 A |
| 3,483,860 | 12/1969 | Namerow | 128/653 |
| 4,135,131 | 1/1979 | Larsen et al. | 128/653 |
| 4,297,708 | 10/1981 | Vidal | 343/754 |
| 4,320,404 | 3/1982 | Chekroun | 343/754 |

FOREIGN PATENT DOCUMENTS

| 2224887 | 10/1974 | France | 343/754 |
| 2448792 | 6/1980 | France | 343/754 |

*Primary Examiner*—Eli Lieberman
*Assistant Examiner*—K. Ohralik
*Attorney, Agent, or Firm*—Pollock, VandeSande & Priddy

[57] ABSTRACT

This invention relates to a process and means for rapid microwave imaging using UHF waves transmitted by an antenna toward a body to be scanned. According to the invention, body O to be scanned is placed in front of a transmitting antenna A and various signals forming the various points of the image are analyzed in a collector-unit RC consisting of a diode-conductor panel 1 and a wave-guide stack 2 and are then transmitted to a receiver R.

5 Claims, 5 Drawing Figures

PROCESS AND MEANS FOR RAPID POINT BY POINT SURVEY OF BODY SCANNING RADIATION FIELD

This application is a continuation-in-part of application Ser. No. 394,986, filed July 2, 1982.

FIELD OF THE INVENTION

This invention relates to a process and device for achieving rapid point by point survey of a radiation field having passed through a body.

SUMMARY OF THE INVENTION

Recent work has been oriented toward obtaining images of objects illuminated by UHF waves. Attempts have been made in particular in bio-medicine. If an organ is put under UHF radiation, it is possible to obtain an "image" if a probe for analyzing the wave received (transmitted or "diffracted" by the organ) is moved behind the organ to be scanned.

This method has not yet resulted in effective and practical applications because of the following difficulties.

(1) The energy measured directly by the probe moved behind the object is very weak, which leads to a poor quality image because of the high level of "noise".

(2) To obtain an image of relatively satisfactory definition, a great number of precise measurements must be taken. Apart from the fact that this entails the first difficulty mentioned above, it also means much too long a test, easily exceeding an hour, which is impossible in practice and medically counter-productive.

(3) If the above-mentioned difficulties were to be solved by increasing the number of test probes, the design of the device would quickly become very expensive and pose numerous technical problems.

BRIEF DESCRIPTION OF THE INVENTION

This invention proposes a process and device enabling the above-mentioned difficulties to be solved while at the same time enabling one to produce good microwave images of objects, with the invention being particularly applicable to bio-medicine and industry.

The process of rapid microwave imaging using UHF waves transmitted by an antenna toward the body to be scanned is characterized under the invention in that the following are placed in succession:

a UHF transmitting antenna;
the body to be scanned;
a collector-unit collecting waves received through said body, with said unit enabling sampling of the transmitted wave at an interval smaller than the wavelength being used.

The device of the invention is characterized in that it comprises:

a UHF transmitting antenna,
a collector-unit located at a certain distance from the antenna for collecting waves received from the antenna, with the space between the antenna and the unit being sufficiently able to accommodate the body to be scanned, said unit comprising:
   a panel (in itself known) consisting of direct conductors and conductors equipped with diodes disposed in parallel and in alternation, one after the other, parallel to the component to be measured of vector $\vec{E}$ of the transmitted wave, at a distance which is less than the wavelength used, with said panel comprising means of blocking (or reverse polarizing) all diode-conductors except one, which is sequentially variable in position;
   a stack of waveguides constituting focusing lenses, located at a short distance behind this panel, said guides being spaced apart at an interval smaller than the wavelength,
means for collecting separately the signals received at each wave-guide.

The invention produces a point by point survey of a radiation field which has passed through a body. The image processing of the surveyed field is achieved by prior art methods, such as computerized graphics terminals, which do not, per se, form a part of the invention.

Figure 2:
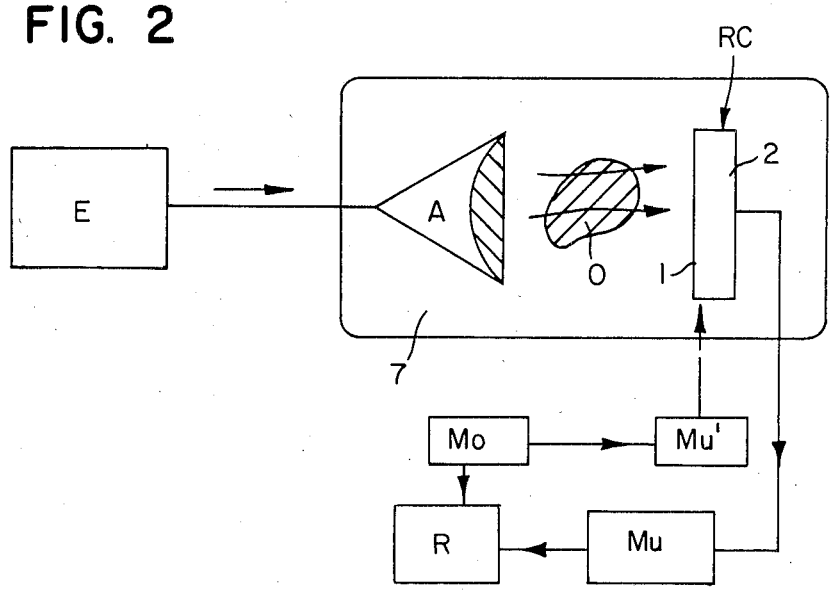
Figure 3:
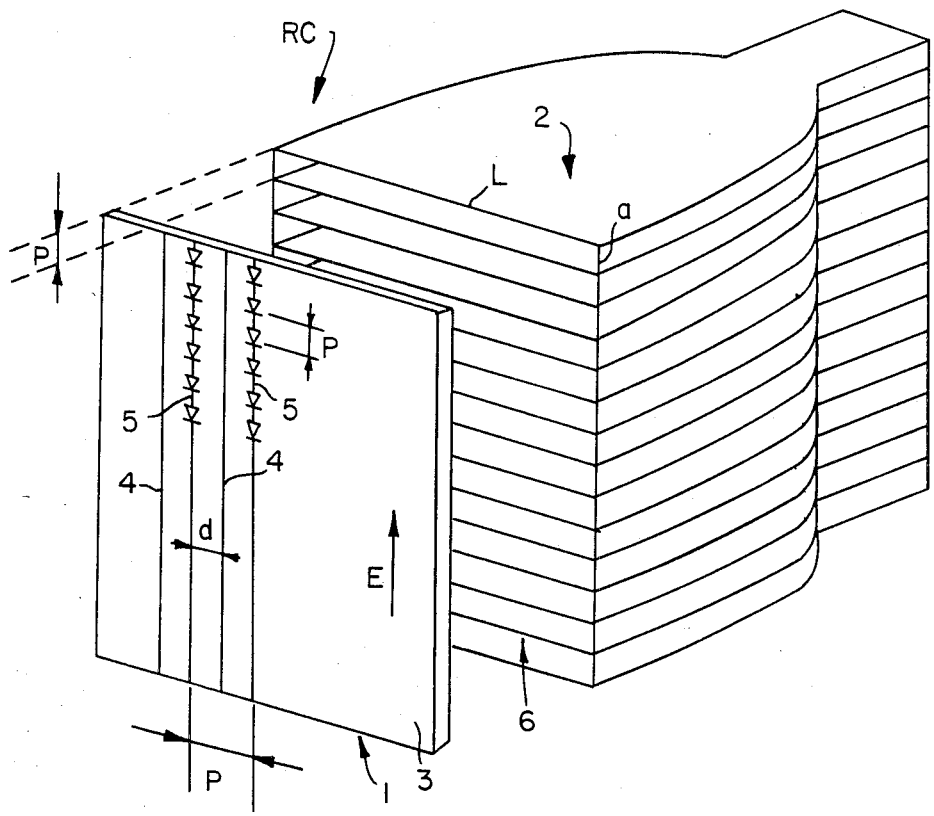
Figure 4:
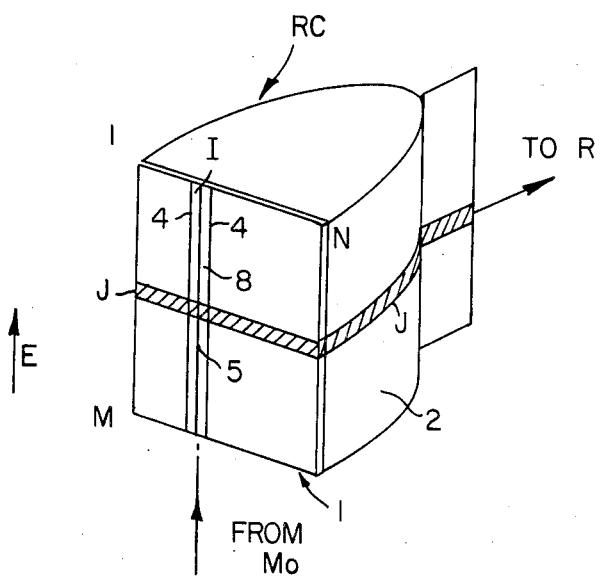

This invention and its application will be clarified by the following description, made with reference to the attached drawings in which:

FIG. 1 is a schematic view of the general principle of microwave imaging known from the prior art, FIG. 2 is a diagram showing more precisely how the microwave image of an organ is constructed utilizing the inventive point by point survey of a radiation field after passing through an organ, FIG. 3 shows schematically in perspective and exploded view how a collector-unit can be constructed according to the invention, FIG. 4 shows on a smaller scale and schematically how the collector-unit of the imaging device of the invention is used.

Figure 5:
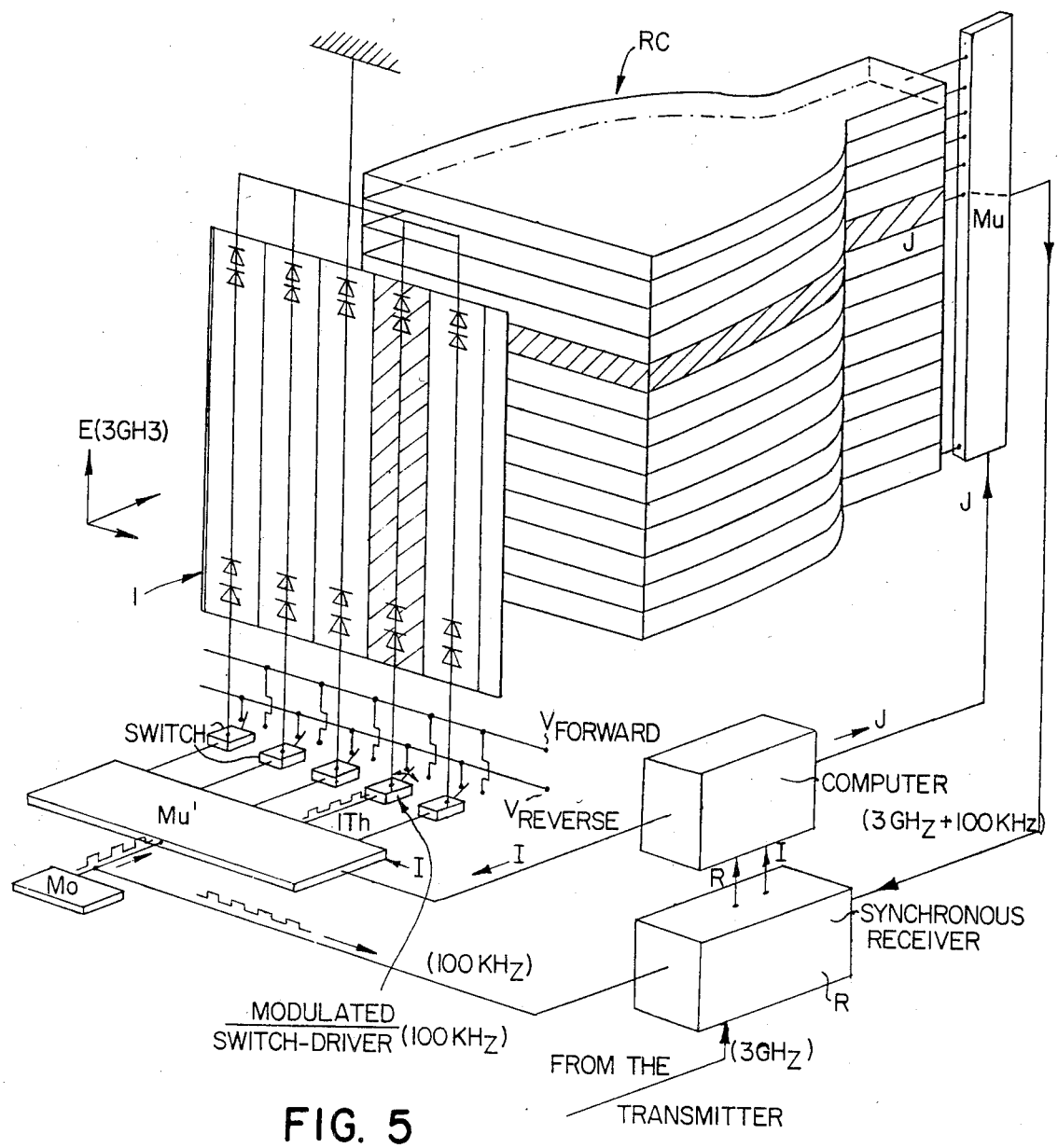

FIG. 5 is a more detailed perspective schematic diagram of the present invention.

Reference is made first to FIG. 1, which illustrates the general principle that various works have attempted to apply in the prior art.

A UHF antenna A transmits from a transmitter E in the direction of an organ O to be scanned. Behind organ O, a probe S connected to a receiver R is moved.

In this procedure, the test is much too slow, requiring several hours.

Reference is next made to FIG. 2 which shows the principle of application of the invention.

Body O to be scanned is placed in front of an antenna A supplied by its transmitter E. Waves passing through organ O fall onto a collector-unit RC the organization and operation of which are described below with reference to FIGS. 3 and 4.

Reference is now made to FIG. 3 which shows one embodiment of collector-unit RC. This unit consists essentially of two parts, i.e., a panel 1 forming the "retina" of the device, and a stack of wave-guides 2 constituting a collector.

Panel 1 is of a type known and described in U.S. Pat. No. 3,708,796 issued Jan. 2, 1973, to Bony Gilbert. As shown in FIG. 3, this panel comprises a network of direct electric conductors 4 or diode-equipped conductors 5 spanning a dielectric support plate 3 parallel to electric field vector $\vec{E}$ component used for the test. To avoid crowding FIG. 3, and also because the panel in question is known, only two direct conductors 4 and two diode-conductors 5, on which only a few diodes appear, are shown here. The diode-conductors can be supplied, as described in the patent mentioned above, in such way that all of the diodes on a wire will either conduct or block. If proper spacing d and P between succesive adjacent direct conductors and diode-conductors is observed, and if a certain spacing between diodes p on the conductors is observed, waves received on this panel will pass through it without loss or distorton, if the diodes are blocked (or reverse polarized), or will reflect the wave received, if the diodes conduct (or are direct polarized). Values P, p and d are essentially a function of the transmission wavelength, of the construction characteristics of the panel, and of the diodes' capacities. For example, working with 3 GHz frequency, which in water corresponds to a wavelength of about 11 millimeters, satisfactory results are reached by taking p=2.5 mm (or about $\lambda/4$), P=2d=5 mm (or about $\lambda/2$) with PIN type diodes having capacities of the order of 0.4 pf.

Behind panel 1 is placed a stack of wave-guides 2 whose small side a is parallel to conductors 4, 5 and vector $\vec{E}$, and whose large side L is orthogonal to conductors 4, 5. In operation, panel 1 is pressed against input surface 6 of stack 2 forming the collector. Side a of each guide is advantageously equal to diode spacing interval p, or, in the example mentioned above, a=2.5 mm.

The shape of each wave-guide is set so as to obtain, in the transmitting state, an aperture field having uniform distribution of phase and amplitude at their opening. For example, an exponential shape enables an aperture field to have uniform distribution both in amplitude and phase difference, simulating a lens effect. Guides are adapted according to the radiation medium 7 (see FIG. 2) which is usually water if the application is to be bio-medicine. Adaptation can be made by introducing into the guide opening a dielectric plate of appropriate thickness.

The device is to be used as follows.

All diode-conductors but one are polarized in reverse, thereby isolating (as drawn in FIG. 4) a section of panel 1 parallel to electric field vector $\vec{E}$ constituting an opaque window 8 between the two direct conductors 4 which surround the only direct polarized diode-conductor 5. Thus collector 2 picks up, at the level of each wave-guide making it up, a modification of the signal corresponding to the field in this window. Each guide can be connected to a separate receiver, enabling analysis of the signal characteristics corresponding to each small rectangular sector of intersection of window 8 along row i and of the wave-guide along row j. In a variant, as shown in FIG. 2, only one receiver R is provided to receive all of the signals proceeding from the stacked waveguides, with a multiplexer Mu being inserted to ensure successive reading of the signals within each guide of the stack (I-m).

To improve the reading of the signal, direct-reverse switching of diode-conductor 5 of window 8 is modulated by a modulator Mo. Multiplexer Mu' assures successive addressing of the various windows 8 from the first to the last (I-n).

In one embodiment, a stack of thirty-two waveguides and a juxtaposition of thirty-two windows such as window 8 were used, enabling an image consisting of one thousand twenty-four points to be created. If a multiplexer such as Mu, connected to receiver R, is used, an image can be obtained within approximately one second. Of course, if thirty-two receivers are used, i.e., one per guide, the image can be obtained within less than a thirtieth of a second.

FIG. 5 illustrates in greater detail the interconnection between components of the present invention. The emitting antenna generates an electromagnetic wave which, for example, may be 3 GH$_z$. The electromagnetic field vector E propagates through a surrounding medium and impinges upon a body undergoing tests (FIG. 2).

The body may be larger or smaller than the incident beam section. The result will be either a hole or partial image of the body. The impinging radiation wave is subsequently scattered by the body and the electromagnetic field at the output of the body produces differences when compared to the condition when a body is absent. The differences of the electromagnetic field are typical of the interaction between an electromagnetic field and a body and after measurement, recording and mathematical computation which does not, per se, form part of the present invention, a tomographic image of the whole body or part of it is possible.

If among the diode-conductors (diode columns) one is selected by the multiplexer Mu' (Ith diode conductor), the diodes are alternately reverse and forward biased at a relatively low frequency, for example 100 Kh$_z$. This occurs due to the introduction of the low frequency by modulator M$_o$. The signal received by each of the stacked wave guides is partly modulated at the low frequency. The modulation of the signal is proportional to the existing field at the location of the diode immediately located in front of the aperture of the stacked waveguide. If at the output of the Jth waveguide, chosen through the second multiplexer Mu, we extract the low frequency component by means of receiver R and we obtain a voltage proportional to the electromagnetic field at the crossing of the Ith column of the diode-conductors and the Jth row of the waveguide stack. Combining each of these orthogonal crossings, it is possible to record the field at all points of the panel 1. It is to be emphasized that the invention relates to the point by point measurement of the radiation field after passing through a body. The generation of an image from such measurements is achieved by conventional data analysis techniques including prior art computerized image processing which need not be explored herein.

We claim:

1. A system for rapid and point by point survey of a UHF radiation field having passed through a body, the system comprising:

an antenna for transmitting UHF radiation to the body undergoing scanning;

a stack of waveguides having coplanar apertures and positioned in radiation alignment with the antenna and at a distance therefrom sufficient for location of the body between the antenna and the stack, adjacent individual waveguides being spaced at a distance less than one wavelength;

a panel having a plurality of parallel alternating columns of conductors and serially connected diodes biased in the same direction, adjacent diode columns being less than one wavelength apart;

the columns being positioned parallel to the component of a radiation field vector to be measured;

means for reverse biasing all of the diode columns except a single selected forward biased diode column thereby polarizing the selected diode column to impinging radiation;

means for producing a signal in relation to the electromagnetic field at the orthogonal crossing of a selected column in the panel and a selected row in the stack of waveguides, which corresponds to a scanned point which is in registry with the orthogonal crossing.

2. The system set forth in claim 1 together with a multiplexer connected at its output to each of the diode columns; and means connected to an input of the multiplexer for providing a modulation signal thereto; and
  switching means connected between the multiplexer output and the diode columns for providing a modulated forward-back biasing signal to the diode columns.

3. The system set forth in claim 2 wherein each diode column becomes sequentially polarized with each waveguide of the stack for producing signals corresponding to individual points of a scanned body.

4. A method for rapidly measuring, on a point by point basis, the radiation field having passed through a body, the steps comprising:
  (a) transmitting radiation from an antenna to a body undergoing scanning;
  (b) positioning a stack of waveguides having coplanar apertures in radiation alignment with the antenna and at a distance therefrom sufficient for location of the body between the antenna and the stack;
  (c) locating adjacent individual waveguides at a distance less than one wavelength apart;
  (d) positioning a diode array panel between the body and the waveguides, the panel having a plurality of parallel alternating columns of conductors and serially connected diodes biased in the same direction, adjacent diode columns being less than one wavelength apart;
  (e) positioning the columns parallel to the component of a radiation field vector to be measured;
  (f) reverse biasing all of the diode columns except a single selected forward biased column thereby polarizing the selected diode column to impinging radiation; and
  (g) producing a signal in relation to the electromagnetic field at the orthogonal crossing of a selected diode column in the panel and a selected row in the stack of waveguides, which corresponds to a scanned point which is in registry with the orthogonal crossing;
  (h) sequentially repeating steps (f) and (g) until all the orthogonal crossings between the diode columns and waveguides in the stack have been scanned.

5. The method set forth in claim 4, wherein the antenna, body to be scanned, and waveguide stack are placed in the same ambient medium having a dielectric constant which is similar to that of the scanned body.

* * * * *